United States Patent [19]

Konings et al.

[11] Patent Number: 5,684,060
[45] Date of Patent: Nov. 4, 1997

[54] COMPOSITIONS CONTAINING INORGANIC, ORGANIC AND ORGANOMETALLIC PALLADIUM HYDROGEN SCAVENGERS

[75] Inventors: Mark S. Konings; Joel D. Oxman, both of Minneapolis, Minn.

[73] Assignee: Minnesota Mining and Manufacturing Company, St. Paul, Minn.

[21] Appl. No.: 629,864

[22] Filed: Apr. 9, 1996

[51] Int. Cl.$^6$ ........................................ A61K 6/10
[52] U.S. Cl. ..................... 523/109; 524/785; 528/15; 264/16; 264/19; 523/103
[58] Field of Search ............... 264/16, 19; 528/15; 524/785; 523/109, 103

[56] References Cited

U.S. PATENT DOCUMENTS

| 4,273,902 | 6/1981 | Tomioka et al. | 525/478 |
|---|---|---|---|
| 4,359,565 | 11/1982 | Puppe et al. | 528/15 |
| 4,957,667 | 9/1990 | Hamer | 264/16 |
| 5,258,435 | 11/1993 | Huggins | 524/357 |

FOREIGN PATENT DOCUMENTS

| A-0046907 | 3/1982 | European Pat. Off. . |
|---|---|---|
| A-0464918 | 1/1992 | European Pat. Off. . |
| A-0668325 | 8/1995 | European Pat. Off. . |

*Primary Examiner*—Melvyn I. Marquis
*Attorney, Agent, or Firm*—Gary L. Griswold; Walter N. Kirn; Dale A. Bjorkman

[57] ABSTRACT

The present invention provides an addition-curable composition containing an inorganic, organic or organometalic compound of palladium in an amount effective to reduce the amount of hydrogen gas evolved in the reaction of the composition. A preferred embodiment is a dental impression material composition comprising: (a) an addition-curable compound; (b) a crosslinker; (c) a platinum-containing catalyst; and (d) a palladium compound. This generally provides a positive gypsum model of, for example, a dental impression that is substantially free of pits.

34 Claims, No Drawings

COMPOSITIONS CONTAINING INORGANIC, ORGANIC AND ORGANOMETALLIC PALLADIUM HYDROGEN SCAVENGERS

FIELD OF THE INVENTION

This invention relates to inorganic, organic and organometallic palladium compounds which are useful as hydrogen scavengers in curable compositions from which hydrogen is evolved. The invention is particularly useful in absorbing hydrogen released from addition-curable silicone dental impression material compositions. The absorption of released hydrogen may decrease significantly imperfections or pits in the positive model made from the impression.

BACKGROUND OF THE INVENTION

Many addition-curable compositions, particularly addition-curable silicone dental compositions, release hydrogen gas as a byproduct of the reaction of an organopolysiloxane and an organohydrogenpolysiloxane in the presence of a catalyst. The hydrogen gas evolution may cause undesirable imperfections or pits in a material subsequently applied to or poured into the dental impression (i.e., negative model) to form a positive model. This may result in the formation of an article which is unacceptable or, in the case of a dental device, does not fit properly.

U.S. Pat. No. 4,273,902 describes the use of finely divided palladium metal powder, palladium alloys or palladium metal deposited onto a support as hydrogen scavengers in addition-cure silicone impression material formulations.

U.S. Pat. No. 4,957,667 describes the use of finely divided palladium applied over at least a portion of the negative impression material before pouring the hardenable positive impression material or admixture of finely divided palladium with the positive impression material prior to pouring.

SUMMARY OF THE INVENTION

The present invention relates to compositions comprising (a) an addition-curable compound, e.g., vinyl-containing organopolysiloxane; (b) a crosslinker, e.g., an organopolysiloxane containing a multiplicity of SiH bonds; (c) a platinum containing catalyst, e.g., a platinum containing hydrosilation catalyst; and (d) a compound of palladium in an amount effective to reduce the amount of hydrogen gas evolved in the reaction of said composition. Preferably, the composition exhibits a Hydrogen Gas Evolution Value in 2 hours per 10.0 g of the composition of less than about 0.6 mL. Preferably, the positive gypsum model formed from the composition will be substantially free of pits.

For the purposes of the present invention, the term "palladium compound" means a chemical entity in which palladium is bonded to an inorganic, organic or organometallic moiety or any combination thereof.

The present invention also relates to a method of making a positive dental model comprising the step of preparing an impression using a hardenable composition, said composition comprising (i) an addition-curable compound; (ii) a crosslinker; (iii) a platinum containing catalyst; and (iv) a palladium compound in an amount effective to reduce the amount of hydrogen gas evolved in the reaction of said composition. Preferably, the composition contains an amount of palladium compound such that the Hydrogen Gas Evolution Value in 2 hours per 10.0 g of the composition is less than about 0.6 mL.

The invention also relates to a method of making a positive dental model comprising the step of applying a palladium compound over at least part of the surface of an impression that will contact a positive model material before pouring said model material.

The present invention also relates to a method of making a positive dental model comprising the step of scavenging hydrogen gas escaping from an impression by mixing a palladium compound with a hardenable positive model material prior to pouring said model material.

DETAILED DESCRIPTION OF THE INVENTION

The present invention provides a novel solution to providing a substantially pit-free positive model of a curable composition from which hydrogen gas is evolved. In a preferred embodiment, the curable composition comprises a dental impression making system which comprises incorporating a palladium compound in the composition material, applying a palladium compound to at least a portion of the surface of the impression, incorporating a palladium compound in the positive model material prior to pouring the model material into the impression or any combination thereof.

A preferred embodiment of the invention comprises a dental impression material composition comprising: (1) an addition-curable compound comprising a vinyl-containing organopolysiloxane; (2) a crosslinker comprising an organopolysiloxane containing a multiplicity of SiH bonds; (3) a platinum containing catalyst capable of catalyzing a hydrosilation reaction; and (4) a palladium compound. The palladium compound scavenges some or all of the hydrogen evolved as a byproduct of the hydrosilation reaction.

The amount of the palladium compound should be sufficient to scavenge the hydrogen gas released from an addition-curable composition in which it has been incorporated and can be determined by gas chromatography ("GC") in the Hydrogen Gas Evolution Value test described below. Preferably the amount of hydrogen evolved in 2 hours per 10.0 g of impression material is less than about 0.6 mL, more preferably less than about 0.4 mL and most preferably less than about 0.2 mL. Preferably, the palladium compound is present in a silicone impression material in an amount from about 1 to about 500 ppm, more preferably from about 5 to 300 ppm and most preferably from about 10 to 200 ppm of the total composition based on palladium as the element.

The effectiveness of the palladium compound in scavenging the hydrogen can be determined, in a practical sense, by inspection of a positive gypsum model formed from the impression. The positive model is substantially free of pits when the gypsum is poured into the impression preferably in less than about 2 hours, more preferably in less than about 30 minutes and most preferably in less than 5 minutes after the start of extrusion of the impression material. Although the hardening or set time of the gypsum model material from the start of mixing with water will vary depending on the manufacturer and type of gypsum, the hardening time is generally about 30 minutes to one hour.

An advantage of the use of a palladium compound rather than palladium metal or alloy in one or more components of a dental impression making system, especially an addition-curable silicone impression material, is that a lesser quantity of palladium compound is required to provide a positive model with an equivalent reduction in the number of pits observed compared with the use of an equal amount of palladium metal or alloy. This is significant since palladium compounds as well as palladium metal or alloy are rather costly materials. Also many palladium compounds are soluble in silicone compositions and as such may decrease the likelihood of separation of the palladium compound from the silicone composition on storage. Palladium metal powders, on the other hand, are insoluble and very dense and may become unevenly dispersed in the formulation and give erratic performance characteristics in terms of hydrogen scavenging capability. This problem may be exacerbated in unfilled impression material formulations, The term "silicone," as used herein, refers to a polymer having, for the most part, alternating silicon and oxygen atoms (i.e., a polysiloxane chemical structure) and having sufficient pendant functional groups to undergo a setting reaction in the presence of a crosslinker compound and a catalyst compound.

The term "crosslinker," as used herein, refers to polymers that react with the functional group or groups of the polymer chains (e.g., $R^1$ and $R^2$ of formula F1) simultaneously to lengthen them and connect them laterally, e.g., to form the crosslinked network characteristic of a silicone elastomer. In contrast to a thermoplastic polymer (i.e., a polymer that softens and flows upon heating) a crosslinked polymer, after crosslinking, is incapable characteristically of further flow.

The term "hydrosilation" (alternatively, spelled "hydrosilation") means the addition of an organosilicon hydride compound to a compound containing an aliphatic multiple bond (e.g., an olefinic or acetylenic unsaturation), preferably a vinyl group, $—CH=CH_2$.

As used herein, "solubility" means the capability of a substance to form a solution, i.e., either a true solution or a colloidal solution. A true solution is a uniformly dispersed mixture at the molecular or ionic level of one or more substances (the solute) in one or more substances (the solvent). A colloidal dispersion is often called a solution. Since colloidal particles are larger than molecules it is strictly incorrect to call such dispersions solutions; however, this term is widely used in the literature, especially when the mixture is only slightly milky. As used herein, "dispersibility" means the capability of a substance to form a dispersion, i.e., a two-phase system where one phase consists of finely divided particles (often in the colloidal size range) distributed throughout a bulk substance, the particles being the disperse or internal phase and the bulk substance the continuous or external phase.

The present invention provides compositions (e.g., silicone compositions) which are useful for preparing sealants, caulks, adhesives, coatings, impression materials, molding materials, lithographic plates, release liners, potting materials and reflective sheets. Preferred applications of this invention include areas in which non-stick or low-energy properties of a surface are required such as impression materials, modeling materials or in release coatings for use with pressure-sensitive adhesives.

Optional ingredients of the compositions of the invention include fillers (e.g., pulverized metals, silica, quartz, calcium carbonate or metal oxides), appropriate polymerization initiators and inhibitors, pigments, stabilizers, surfactants, modifying agents and copolymerizable and non-copolymerizable cosolvents, and the like.

Preferred dental impression materials of the present invention comprise between about 0 and 90 weight percent filler, more preferably between about 20 and 80 weight percent filler, and most preferably between about 30 and 75 weight percent filler.

The dental impression material compositions of the invention are generally pre-mixed into preferably two pans prior to use. For example, part "A" may contain the vinyl-containing organopolysiloxane, the platinum catalyst and the palladium compound, while part "B" may contain the organohydrogenpolysiloxane crosslinker and optionally vinyl-containing organopolysiloxane. Alternatively, the palladium compound may be incorporated in part "B" and not in part "A," or may be in both parts "A" and "B." It is presently preferred to have the palladium compound in part "A." At the time of use, the two parts may be combined by mixing them together manually, kneading the two pastes together or using a static or mechanical mixer.

In practice, the impression material generally is syringed through a static mixing device into an impression tray and placed in the patient's mouth. After the impression material is set, the tray is removed from the patient's mouth and, in instances where the dental practitioner prepares the positive model, it may be preferable to pour the positive model material immediately after removal of the impression from the patient's mouth. It is more preferable to disinfect the impression prior to pouring the model material. Although it is generally referred to as "immediate pour," in a practical sense, this means that the positive model material is poured into the impression in less than about 5 minutes. When this is the case, generally insufficient time has elapsed to allow the hydrogen gas to dissipate from the surface of the impression material and an unacceptable number of pits may be present in the positive model. More frequently, the positive model material is poured into the impression in about 30 minutes to 2 hours after making the impression.

In a preferred embodiment, a palladium compound is added to the curable silicone composition to scavenge the hydrogen evolved from the hydrosilation reaction which takes place when the two parts of the silicone impression material are admixed. The evolution of hydrogen gas is a problem because the step after making an impression is forming a positive model by filling the impression with a material such as plaster of Paris (i.e., gypsum), wax or epoxy. If hydrogen gas is evolving, bubbles form at the surface of the impression material which result in pits in the subsequently poured and hardened gypsum. Alternatively, a palladium compound may be applied to at least a portion of the surface of the impression or incorporated in the positive model material prior to pouring the model material into the impression.

The addition-curable compounds of the invention generally are synthetic polymeric silicone materials that possess an extraordinarily wide range of physical properties. They can be low- or high-viscosity liquids, solid resins, or vulcanizable gums. They display an unusual combination of organic and inorganic chemical properties that are due to their unique molecular structure of alternating silicon and oxygen atoms. Suitable silicone polymers are well-known in the art and are described, for example, in "Silicones," *Kirk-Othmer Encyclopedia of Chemical Technology*. 3rd Ed., 20, 922–962 (1982). The typical polymeric silicone material is a siloxane polymer depicted below in formula F1.

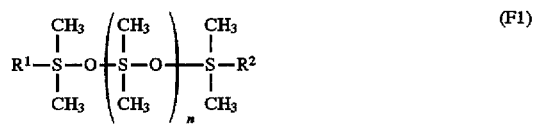 (F1)

These silicone polymers may be made by an equilibrium process from other siloxanes and typically n is a value selected such that the polymers range in viscosity from about 0.01 Pa s to 2500 Pa s. Silicone polymers can be mixed with other chemicals and fillers into an enormous variety of products that serve in a multitude of applications.

Vulcanizing silicones are a special class of silicones that have as a common attribute the development of a crosslinked elastomer from relatively low molecular weight polymers by means of a chemical reaction that forms these crosslinks and effectively extends chain length simultaneously. An essential ingredient in a vulcanizing silicone is a crosslinking component (hereinafter the "crosslinker" or "organohydrogenpolysiloxane") that reacts with the "functional group" or groups (e.g., $R^1$ and $R^2$ of formula F1) of the polymer chains simultaneously to lengthen them and connect them laterally to form the crosslinked network characteristic of a silicone elastomer. Usually a catalytic agent is included to facilitate the reaction of the crosslinker with the polymer's functional groups.

A particularly preferred addition-curable composition comprises a silicone formed by reacting (1) a multiply-vinyl-containing organopolysiloxane with (2) an organopolysiloxane containing a multiplicity of SiH bonds per molecule (i.e., an organohydrogenpolysiloxane). This reaction is typically facilitated by the presence of (3) a platinum catalyst of the Karstedt type. Platinum catalysts of the Karstedt type are described in U.S. Pat. Nos. 3,715,334, 3,775,452 and 3,814,730 which are herein incorporated by reference.

The setting reaction of an addition-curable silicone is triggered, in general, by the mixing together of the addition-curable compound, the crosslinker and the catalyst. By varying the amount of crosslinker and catalyst, the rate of setting may be adjusted. The rate of setting may be adjusted further by the incorporation of well known inhibitors and/or retarders. One such inhibitor is 1,3,5,7-tetramethyl-1,3,5,7-tetravinylcyclotetrasiloxane. These retarders often operate by reacting competitively with the catalyst, thereby slowing the crosslinking reaction.

Suitable addition-curable compounds for use in the present invention include ethylenically unsaturated compounds which undergo a crosslinking reaction with a crosslinker in the presence of a hydrosilation catalyst. Typically, the crosslinking reaction is facilitated by a catalyst compound and may be affected by temperature (e.g., the reaction may proceed at a somewhat greater rate at an elevated temperature or alternatively may be initiated at an elevated temperature). Preferred ethylenically unsaturated compounds include monomers, oligomers or polymers which comprise pendant or terminal ethylenically unsaturated groups, such as vinyl, alkenyl or cycloalkenyl groups, that react with the crosslinker in the presence of a catalyst. Alternatively, the functional group(s) may be situated along the polymer chain (i.e., along the backbone) and not be in a pendant position. Of these ethylenically unsaturated groups, vinyl groups are more preferred, and terminal vinyl groups are most preferred. In general, the cured composition's backbone network or structure comprises both the formerly ethylenically unsaturated compound and the crosslinker. Either compound could be employed in greater or lesser proportion or have greater or lesser initial molecular weight. Furthermore, depending on the combination of ethylenically unsaturated compound and crosslinker, one could utilize a broad variety of backbones in these compounds and thereby achieve a broad variety of cured compositions having a wide range of physical properties.

Addition-curable compounds containing aliphatic unsaturation which are useful in the present invention have olefinic or acetylenic unsaturation. These compounds are well-known in the art of hydrosilation and are disclosed in such patents as U.S. Pat. No. 3,159,662 (Ashby), U.S. Pat. No. 3,220,972 (Lamoreaux), and U.S. Pat. No. 3,410,886 (Joy) which are herein incorporated by reference. Additional particularly useful unsaturated compounds which contain silicon are disclosed in U.S. Pat. No. 4,916,169 (Boardman et al.) which is herein incorporated by reference. The preferred molecular weight of the organopolysiloxane often depends upon the desired viscosity of the composition prior to crosslinking. In general, as the molecular weight is increased the viscosity of the uncrosslinked composition increases correspondingly. For uses as molding compositions, the average value of n in formula (F1) preferably is between 10 and 6000, more preferably between 50 and 2000 and most preferably between 100 and 1000. Mixtures of more than one molecular weight may also be utilized.

The groups $R^1$ and $R^2$ of formula (F1) represent the "terminal" portions of the polymer chain and are often the sites for the attachment of functional groups, i.e., groups which participate in the crosslinking reaction. It is also contemplated that one or more sites depicted in formula (F1) as having non-functional methyl groups might instead contain a functional group and that $R^1$ and/or $R^2$ then may comprise a non-functional group such as a methyl group or another monovalent hydrocarbyl or halogenated monovalent hydrocarbyl group as listed below. Therefore, formula (F1) is intended merely to illustrate a "typical" organopolysiloxane polymer with terminal functional groups. The site of attachment of the two or more functional groups may be varied as desired and is not believed presently to be of essential importance to the practice of the present invention. The two or more functional groups are in general unsaturated aliphatic groups having 2 to 20 carbon atoms, such as alkenyl groups including vinyl, allyl, butenyl, propenyl, isopropenyl, and hexenyl groups or cycloalkenyl groups including cyclohexenyl, cyclopentenyl, cycloheptenyl and cyclooctenyl groups. A preferred unsaturated aliphatic group is vinyl. Most preferably, both $R^1$ and $R^2$ are vinyl groups and are located in terminal positions as depicted in formula (F1).

When special properties are needed, other non-functional monovalent hydrocarbyl and halogenated monovalent hydrocarbyl groups may be substituted for the methyl groups of formula (F1). For example, alkyl groups having 1 to 18 carbon atoms, e.g., methyl, ethyl, propyl, butyl, hexyl, dedecyl, octyl, and octadecyl; cycloalkyl groups having 5 to 7 ring carbon atoms, e.g., cyclohexyl and cycloheptyl; aryl groups having 6 to 18 carbon atoms, e.g., phenyl, naphthyl, tolyl, xylyl; aralkyl groups including benzyl, β-phenylpropyl, β-phenylethyl, and naphthylmethyl; alkoxy groups having 0 to 18 carbon atoms such as hydroxy, methoxy, ethoxy, and dodecyloxy; and halo-substituted hydrocarbon groups such as dibromophenyl, chloromethyl, 3,3,3-trifluoropropyl and chlorophenyl may be employed in place of all or some of the methyl groups of formula (F1).

Another addition-curable compound useful in this invention is a branched organopolysiloxane having the general formula:

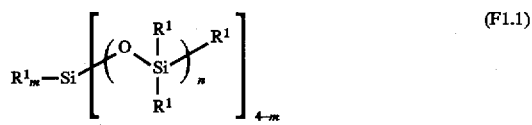

(F1.1)

wherein each $R^1$ is a functional group or a nonfunctional group as defined above and wherein at least two but preferably not more than one-half of all the $R^1$ groups in the siloxane are functional groups, m represents 0, 1, 2, or 3, and n represents a number having an average value from 1 to about 10,000. Compounds containing more than one branch point as depicted in formula (F1.1) may also be employed.

Another class of suitable addition-curable compounds useful as ethylenically unsaturated siloxane polymers in this invention and which contain the functionality described in formula (F1.1) are the MQ resins. These polymers contain tetrafunctional $SiO_{4/2}$ (Q units) and $R^aR^bR^cSiO_{1/2}$ (M units) where the $R^a$, $R^b$, and $R^c$ are vinyl, methyl, phenyl, ethyl, hydroxy, or hydrogen. MQ resins where $R^a$ and $R^b$ are methyl and $R^c$ is vinyl are most suitable for use as ethylenic compounds in this invention. Typically these would not be used as the only ethylenic compound in the formulation, but rather in combination with other ethylenic compounds, especially the vinyl terminated polydimethylsiloxane polymers shown in formula F1 where $R^1$ and $R^2$ are vinyl. The use of certain of these polymers in dental impression materials is disclosed in U.S. Pat. No. 5,403,885 and in the international patent application WO 93/17654.

The preferred amount of the organopolysiloxane compound will vary depending upon the desired physical properties of the silicone composition (such as the desired uncured viscosity, cured hardness, etc.). In part due to the wide range of acceptable molecular weights for the polymer component and the many types of adjuvants which may be added to the polymer, this amount will vary widely. Based on the total weight of the composition, the presently preferred amount of organopolysiloxane compound is between 5% and 99%, more preferably between 20% and 90%, and most preferably between 20% and 80% by weight.

The crosslinker contains at least two silicon-hydrogen linkages and can be a polymeric compound or a compound that is not polymeric. These compounds are well known in the art and are disclosed, for example in U.S. Pat. Nos. 3,159,662 to Ashby; 3,220,972 to Lamoreaux; and 3,410,886 to Joy.

Some classes of crosslinker having at least two silicon-bonded hydrogen atoms which can be used in the invention are:

(a) organohydrosilanes having the empirical formula,

$$(H)_a(R^3)_bSi_c \quad (F2)$$

wherein each $R^3$ can be the same or different and represents an organic group, preferably selected from the group consisting of monovalent hydrocarbyl groups, monovalent alkoxy hydrocarbyl groups and halogenated monovalent hydrocarbyl groups, c represents an integer having a value at least 1, a represents an integer having a value at least 2, and the sum of a and b equals the sum of 2 and two times c;

(b) organohydrocyclopolysiloxanes having the empirical formula,

$$H_dR^3_e(SiO)_f \quad (F3)$$

wherein $R^3$ is as defined above, f represents an integer having a value from 3 to 18, d represents an integer having a value at least 2 and preferably less than or equal to f, and the sum of d and e equals two times f; and (c) organohydropolysiloxane polymers or copolymers having the empirical formula,

$$(H)_g(R^3)_hSi_jO_{(j-l)} \quad (F4)$$

wherein $R^3$ is as defined above, j represents an integer having a value from 2 to 10,000, g represents an integer having a value at least 2 and less than or equal to j, and the sum of g and h equals the sum of 2 and two times j.

Among the groups represented by $R^3$ include, for example, straight chain and branched alkyl groups having 1 to 18 carbon atoms, e.g., methyl, ethyl, propyl, butyl, hexyl, dodecyl, octyl, and octadecyl, cycloalkyl groups having 5 to 8 ring carbon atoms, e.g., cyclohexyl and cyclooctyl, aryl, aralkyl, and alkaryl groups having 6 to 18 carbon atoms, e.g., phenyl, naphthyl, tolyl, xylyl, benzyl and phenylethyl, and halo-substituted groups thereof, e.g., chloromethyl, chlorophenyl, and dibromophenyl. Preferably, the $R^3$ group includes methyl and phenyl. More preferably, the $R^3$ group is methyl. The $R^3$ group can also be an unsaturated aliphatic group having 2 to 20 carbon atoms, such as alkenyl or cycloalkenyl, e.g., vinyl, allyl and cyclohexenyl. When the $R^3$ group is a group with aliphatic unsaturation, the silicon compound containing silicon-hydrogen linkages can be reacted with itself to form a crosslinked structure or network.

Another compound having silicon-bonded hydrogen used in this invention is a branched organohydrogenpolysiloxane having the general formula:

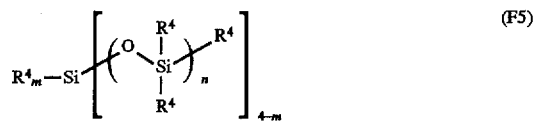

(F5)

wherein each $R^4$ is as defined above for $R^3$ and wherein at least two but preferably not more than one-half of all the $R^4$ groups in the siloxane being hydrogen, m represents 0, 1, 2, or 3, and n represents a number having an average value from 1 to about 10,000. It is understood that compounds containing more than one branch point as depicted in formula (F5) may be employed.

Also useful in the present invention as crosslinkers and which contain the functionality described in formula (F5) are the MQ resins. These polymers contain tetrafunctional $SiO_{4/2}$ (Q units) and $R^dR^eR^fSiO_{1/2}$ (M units) where the $R^d$, $R^e$, and $R^f$ are vinyl, methyl, phenyl, ethyl, hydroxy, or hydrogen. MQ resins where $R^d$ and $R^e$ are methyl and $R^f$ is hydrogen are most suitable for use as ethylenically unsaturated compounds in this invention. Typically these would not be used as the only crosslinker in the formulation, but rather in combination with other crosslinkers, especially the organohydropolysiloxane copolymers shown in formula (F4).

The amount of the crosslinker should be sufficient to provide the desired degree of crosslinking of the silicone composition. In part due to the wide range of acceptable molecular weights for the addition-curable compound and/or the crosslinker, it is presently believed that this amount is best described in terms of the ratio of SiH groups to functional (e.g., vinyl) groups in the composition. The presently preferred ratio of SiH groups to functional groups ("SiH:F") is between 1:1 and 20:1, more preferably between 1:1 and 10:1 and most preferably between 1.3:1 and 4:1. The presently preferred amount of crosslinker component in the total composition is between 0.2% and 90% by weight, more preferably between 0.2% and 20% by weight and most preferably between 0.2% and 10% by weight.

Suitable hydrosilation catalysts for use in the present invention include those compounds which promote or facilitate the addition reaction between the ethylenically unsaturated groups and the silicon-bonded-hydrogen groups. Examples of suitable catalysts include platinum or platinum compound catalysts exemplified by chloroplatinic acid, a complex of chloroplatinic acid and an alcohol, a complex of platinum and an olefin, a complex of platinum and a ketone, a complex of platinum and a vinylsiloxane, colloidal platinum, a complex of colloidal platinum and a vinylsiloxane etc., palladium, a mixture of palladium black and triphenylphosphine, etc.; or rhodium or rhodium compound catalysts. Also suitable for use in the present invention are radiation activated hydrosilation catalysts. For example, one may employ: ($\eta^4$-cyclooctadiene)diarylplatinum complexes (as described in U.S. Pat. No. 4,530,879, Drahnak, which is herein incorporated by reference); ($\eta^5$-cyclopentadienyl) trialkylplatinum complexes (as described in U.S. Pat. No. 4,510,094, Drahnak, which is herein incorporated by reference); or $\theta^5$ cyclopentadienyl)tri($\sigma$-aliphatic)-platinum complexes and a sensitizer that is capable of absorbing visible light (as described in U.S. Pat. No. 4,916,169, Boardman et al.) with traditional vinylsiloxane polymers and crosslinkers. Platinum or platinum compound catalysts are presently preferred. Alternatively, Pt(II) beta-diketonate complexes as disclosed in U.S. Pat. No. 5,145,886 or the photohydrosilation catalyst systems described in U.S. patent application Ser. Nos. 07/626,904 and 07/627,009 are suitable for use in the present invention.

For dental impression compositions, "Karstedt" type catalysts as described below presently are most preferred. Karstedt platinum catalysts are described in U.S. Pat. Nos. 3,715,334, 3,775,452 and 3,814,730, the disclosures of which are herein incorporated by reference. In general, to produce a Karstedt catalyst, there must be utilized (A) platinum halide, and (B) a complexing material in the form of an unsaturated organosilicon material selected from:

(a) unsaturated silanes having the empirical formula,

 (F6)

where R is free of aliphatic unsaturation and selected from monovalent hydrocarbon radicals, R' is selected from monovalent aliphatically unsaturated hydrocarbon radicals, X is a hydrolyzable radical, c is an integer having an average value of at least 1, b is an integer having an average value greater than or equal to 2, and the sum of a plus b plus z equals the sum of 2 and two times c for a linear or branched silane and the sum of a plus b plus z equals two times c for a cyclic silane;

(b) unsaturated linear or branched siloxanes of the empirical formula,

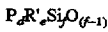 (F7)

where R and R' are as defined above, f is an integer having an average value of between 2 and 10,000, e is an integer having an average value greater than or equal to 2 and the sum of d and e equals the sum of 2 and two times f; and (c) unsaturated cyclic siloxanes of the empirical formula,

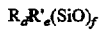 (F8)

where R and R' are as defined above, e is an integer having an average value greater than or equal to 2, f is an integer having an average value from 3 to 18, and the sum of d and e equals two times f.

A Karstedt catalyst can be made by (1) effecting contact between an unsaturated organosilicon material as defined by formula (F6), (F7) or (F8) above, and a platinum halide to provide for the production of a mixture having a concentration of available inorganic halogen, (2) treating the resulting mixture of (1) to effect the removal of available inorganic halogen, and (3) recovering from (2), a platinum-siloxane complex having available inorganic halogen of less than about 0.1 gram atoms of halogen per gram atom of platinum. Preferably the complex is substantially halogen free. As used herein, the term "available inorganic halogen," will designate halogen that can be detected by a modification of ASTM designation D-1821-63 for "Inorganic Chloride." The procedure is substantially as described, except there is utilized in place of acetone a mixture of glacial acetic acid and acetone. The procedure employed for determining gram atoms of platinum in the platinum-siloxane complexes was Atomic Absorption Spectroscopy. For example, the method of R. Dockyer and G. F. Hames, Analyst, 84, 385 (1959).

Radicals included by R in formulas F6, F7, and F8 are, for example, alkyl radicals such as methyl, ethyl, propyl, isobutyl, 2-ethylhexyl, dodecyl, etc.; cycloalkyl radicals such as cyclohexyl, cycloheptyl, etc.; aryl and alkaryl radicals such as phenyl, naphthyl, tolyl, xylyl, and the like; aralkyl radicals such as benzyl, tolylethyl, phenylpropyl, etc. Radicals included by R' in formulas F6, F7 and F8 are, for example, aliphatically unsaturated radicals such as ethynyl, 2-propynyl, etc.; vinyl, allyl, 10-undecenyl, and cycloalkenyl radicals, such as cyclopentenyl, cyclohexenyl, cycloheptenyl, cyclooctenyl, and the like.

Unsaturated silanes included by formula (F6) are, for example, tetravinylsilane, triallylmethylsilane, divinyldimethylsilane, trivinylphenylsilane, divinylmethylphenylsilane, divinylmethylethoxysilane, divinylmethylacetoxysilane, and the like.

Included by the unsaturated siloxanes of formula (F7) are, for example, disiloxanes of the formula,

 (F9)

where R, R', are as defined above, the sum of h and h' is an integer with a value of at least two; the sum of g and h is equal to 3; and the sum of g' and h' is equal to 3. For example, there are included as disiloxanes of formula (F9), 1,1-divinyltetramethyldisiloxane, 1,3-divinyltetramethyldisiloxane, hexavinyldisiloxane, 1,1,3-trivinyltriethyldisiloxane, 1,1,3,3-tetravinyldimethyldisiloxane, 1,3-divinyl,- 1,3-dimethyl,- 1,3-diphenyldisiloxane, etc.

There are also included by the unsaturated siloxanes of formula (F5), cyclopolysiloxanes. For example, there is included 1,3,5-trivinyl-1,3,5-trimethylcyclotrisiloxane, 1,3, 5,7-tetraalkyl-1,3,5,7-tetraphenylcyclotetrasiloxane, 1,3-divinyloctamethylcyclopentasiloxane, etc.

Preferably the above-described platinum-siloxane complexes of platinum and organosiloxanes of formula (F7) and (F5), are made utilizing a platinum halide and an unsaturated linear, branched or cyclic siloxane of formula (F7) or (F5) having at least one structural unit of the formula (F10),

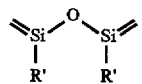 (F10)

where the unsatisfied valences ("Si=") of the above structural unit can be satisfied by R, R' and oxygen radicals and where R and R' are as previously defined. Most preferably R' is a vinyl group.

The platinum halides which can be employed in the practice of the invention are, for example, $H_2PtCl_6nH_2O$ and metal salts such as $NaHPtCl_6nH_2O$, $KHPtCl_6nH_2O$, $Na_2PtCl_6nH_O$, $K_2PtCl_6nH_2O$. In addition, $PtCl_4nH_2O$ and platinous type halides such as $PtCl_2$, $Na_2PtCl_4nH_2O$, $H_2PtCl_4nH_2O$, $NaHPtCl_4nH_2O$, $KHPtCl_4nH_2O$, $K_2PtBr_4$ and platinum halide complexes with aliphatic hydrocarbon as taught in Ashby Pats. 3,159,601 and 3, 159,662, for example [(CH$_2$=CH$_2$)PtCl$_2$]$_2$; (PtCl$_2$C$_3$H$_6$)$_2$, etc. may be employed. Other platinum halides which can be utilized are shown by Lamoreaux Pat. 3,220,972, such as the reaction product of chloroplatinic acid hexahydrate and octyl alcohol, etc.

The amount of the platinum complex catalyst should be sufficient to provide the desired degree of crosslinking of the organopolysiloxane compound within a reasonable time. In part due to the wide range of acceptable molecular weights for the addition-curable compound, it is presently believed that this amount is best described in terms of the ratio of Pt atoms to functional groups in the composition. The presently preferred ratio of Pt atoms to functional groups ("Pt:V") is between 1:2 and 1:2000, more preferably between 1: 10 and 1:1000 and most preferably between 1:30 and 1:500. Preferably, the catalyst is present in an amount from about 5 to about 1000 parts by weight platinum per one million parts by weight of the total composition ("ppm"), more preferably from about 20 to 500 ppm of the total composition.

The palladium compound is incorporated in the composition as a hydrogen scavenger. Suitable palladium compounds include inorganic, organic, and organometallic compounds of palladium, i.e., any compound of palladium wherein palladium is bonded directly to a halogen, oxygen, nitrogen, phosphorus, arsenic, silicon, carbon, or any combination of these elements, or a compound in which palladium is bonded to both a metal and one of the above mentioned elements. A combination of palladium compounds may also be utilized. This does not include palladium metal or metal powders or compounds in which palladium is bonded only to other metals, e.g., palladium-silver or palladium-gold alloys.

Suitable palladium compounds include palladium halides such as palladium (II) chloride, palladium (II) bromide, ammonium tetrachloropalladate (II), and ammonium hexachloropalladate (IV); complexes of palladium and an organic acid such as palladium (II) acetate, palladium (II) propionate, palladium (II) butyrate and palladium (II) trifluoroacetate; complexes of palladium with β-diketones such as palladium (II) acetylacetonate; complexes of a palladium halide and an amine such as trans-dichlorodiammine palladium (II); complexes of palladium and an amine such as diamminepalladium (II) nitrite; complexes of palladium and a phosphine such as bis[1,2-bis(diphenylphosphino)ethane] palladium (0) and tetrakis(triphenyl-phosphine)palladium (0); complexes of a palladium halide with an olefin such as dichloro(1,5-cyclooctadiene)palladium (II) and allylpalladium chloride dimer; complexes of palladium with an olefin such as tris(dibenzylideneacetone)dipalladium (O); complexes of a palladium halide with a nitrogen compound such as dichlorobis-(acetonitrile)palladium (II); and complexes of a palladium halide with a phosphine such as trans-dichlorobis(triphenylphosphine)palladium (II). Additional suitable palladium compounds are described, for example, in F. Albert Cotton and Geoffrey Wilkinson, *Advanced Inorganic Chemistry*, 5th ed., John Wiley & Sons, New York, N.Y. (1988), p. 917–937.

Preferred palladium compounds include palladium halides such as palladium (II) chloride and palladium (II) bromide, complexes of palladium with an organic acid such as palladium (II) acetate, complexes of palladium with β-diketones such as palladium (II) acetylacetonate, complexes of a palladium halide with an olefin such as dichloro (1,5-cyclooctadiene)palladium (II), complexes of a palladium halide with a nitrogen compound such as dichlorobis (acetonitrile)-palladium (II), and complexes of palladium with an olefin such as tris(dibenzylideneacetone) dipalladium (O).

Most preferred palladium compounds include palladium halides such as palladium (II) chloride and palladium (II) bromide, complexes of a palladium halide with an olefin such as dichloro(1,5-cyclooctadiene)palladium (II), complexes of a palladium halide with a nitrogen compound such as dichlorobis(acetonitrile)-palladium (II), and complexes of palladium with an olefin such as tris(dibenzylidene-acetone) dipalladium (0).

The amount of the palladium compound in the composition should be sufficient to absorb all or most of the hydrogen evolved from the hydrosilation reaction. Preferably, the palladium compound is present in an amount from about 1 to about 500 ppm, more preferably from about 5 to 200 ppm and most preferably from about 10 to 100 ppm of the total composition based on palladium as the element.

In the embodiment of the invention wherein the palladium compound is applied to the surface of the impression material, the palladium compound may be applied to the impression surface with or without (i.e., dry) a suspending material such as a solvent. When the palladium compound is applied without a suspending material, preferably the amount of palladium compound used is at least about 0.0001 g/cm$^2$ of impression surface area, more preferably between about 0.0001 and 0.10 g/cm$^2$ based on palladium as the element. The palladium compound may also be adsorbed on a substrate such as carbon, alumina or calcium carbonate. When the palladium compound is applied in a suspending material, the amount of palladium compound in suspension is preferably at least about 0.1% by weight of the suspension, more preferably between about 0.1 and 10.0% by weight based on palladium as the element.

In the embodiment of the invention wherein the palladium compound is admixed with the positive model material (e.g., gypsum), the amount of the palladium compound is preferably at least about 0.05%, more preferably between about 0.1 and 1.0% by weight of the gypsum powder based on palladium as the element. The palladium compound may be either dry or wet (i.e., combined with a suspending material) at the time it is admixed with the gypsum.

HYDROGEN GAS EVOLUTION VALUE

The quantity of hydrogen gas evolved from an addition-curable composition of the present invention was measured at ambient temperature and pressure. Reported volumes were assumed to be at standard temperature and pressure ("STP", i.e., 25° C. and 760 mm Hg) and were not corrected for deviations from STP. Hydrogen standards were prepared over the range to be tested. The first standard was prepared by injecting 0.25 mL of hydrogen gas into a 856.5 mL gas sampling bulb. The bulb was shaken and two injections of 0.5 mL were made within two minutes of each other. A total of four standards were prepared using 0.25, 0.50, 1.00 and 1.50 mL of hydrogen gas and the standard curve was calculated. All samples were analyzed by GC (Hewlet Packard Model 5890, Series II with the thermo conductivity detector and 3396 Series II integrator). The GC was equipped with a 1.8 meter long and 3.2 millimeter diameter stainless steel column packed with Type 5A molecular sieve (60/80 mesh size; Applied Science, Deerfield, Ill.). The injector port temperature was set at 120° C., the column oven and program isothermal at 45° C. and the detector at 200° C. Nitrogen was used as the carrier gas at flow rates of 20 mL per minute on the sample side and 30 mL per minute on the reference side.

Impression material (10.0 g) of each run was extruded through a static mixer onto a tared square of glassine weighing paper. The sample was weighed to the nearest tenth of a gram and immediately placed into a calibrated 1030 mL round-bottom flask equipped wth a stopcock and rubber septum. At a specified time, two 0.5 mL samples of gas were removed from the flask using a 0.5 mL Precision gas-tight syringe (Precision Sampling Corp., Baton Rouge, La.) and injected into the sample side of the GC within 2 minutes of each other.

The following examples are offered to aid in the understanding of the present invention and are not to be construed as limiting the scope thereof. Unless otherwise indicated, all parts and percentages are by weight.

PREPARATOR EXAMPLE

Preparation of a Karstedt Catalyst

A three neck flask was fitted with a mechanical stirrer, reflux condenser, thermometer, and nitrogen purge and placed in a water bath. The flask was charged with 3,000 parts ethanol and 1,200 parts 1,1,3,3-tetramethyl-1,3-divinyldisiloxane and then purged with nitrogen for 5 minutes. Six hundred parts hexachloroplatinic acid was added to the solution and the mixture stirred until the acid was substantially dissolved (about 5 minutes). Eighteen hundred parts sodium bicarbonate was then added over a 5 minute peried. The water bath was heated to 60° C. and then stirred for 2.5 hours. After it had cooled, the solution was filtered, washed with 150 parts ethanol and transferred to a flask containing 6,000 parts dimethylvinylsiloxy terminated polydimethylsiloxane with a viscosity of 0.3 Pa s and a molecular weight of about 10,000 g/mol. The flask was placed on a rotary evaporator and stripped at 45° C. until the vacuum reaches 0.5–1.0 Torr to produce a Karstedt type catalyst solution with a platinum concentration of approximately 2.3–3.0%.

EXAMPLE 1

A stock "catalyst" composition and a stock "base" composition were prepared by combining the ingredients listed in Table 1.

TABLE 1

| Ingredient | Catalyst, parts | Base, parts |
|---|---|---|
| Vinyl-terminated silicone[1] | 48.2 | 32.5 |
| Pt Catalyst[2] | 1.1 | — |
| Si—H crosslinker[3] | — | 13.3 |
| Silwet L-77[4] | — | 0.7 |
| Quso[5] | 6.0 | 6.0 |
| Imsil[6] | 44.0 | 46.0 |
| Inhibitor[7] | — | 0.03 |
| Blue Pigment[8] | — | 1.5 |

[1](Vinyldimethylsiloxy)-terminated polydimethylsiloxane with a viscosity of approximately 2 Pa s; Y-7942 from Witco Corp.; OSi Specialties Group, Danbury, CT.
[2]Karstedt type platinum catalyst of the Preparatory Example.
[3]Organohydropolysiloxane having a viscosity of approximately 50 to 70 mPa s and approximately 0.2% hydride.
[4]Surfactant from Witco Corp.; OSi Specialties Group, Danbury, CT.
[5]Sipernat D13 filler from Degussa Corp., Dublin, OH.
[6]Imsil A-25 microcrystalline silica from Unimen Specialty Minerals, Cairo, IL.
[7]1,3-Divinyltetramethyldisiloxane from United Chemical Technology, Inc., Bristol, PA.

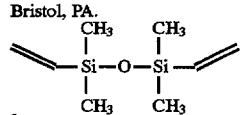

[8]Blue silicone pigment paste SV 1232 from Ferro Corp., South Plainfield, NJ.

For run nos. C-2 through C-5 and 1–15 in Table 2, catalyst pastes containing a palladium additive were prepared by dispersing the amount of the palladium additive indicated in Table 2 in 2.10 g of Silwet L-77 surfactant (1.05 g initially and a 1.05 g rinse). Listed below in Table 2 are the parts of the indicated additive in 300 parts of the catalyst paste and the ppm palladium in the catalyst paste. For each run except C-1, the partially dissolved suspension was placed in an ultrasonic bath for 60–120 minutes, added to 300 grams of stock catalyst composition and mixed for 20 minutes in a Ross double planetary mixer. All palladium additives in Table 2 were obtained from Strem Chemicals, Inc., Newburyport, Mich. Run no. C-1 in Table 2 contained no palladium additive.

For each run, approximately equal volumes of the catalyst and the base compositions were transferred to independent chambers of a dual barrel mixing cartridge which were sealed with inserts. The cartridge was inserted into a hand held dispensing apparatus, a Kenics static mixing tip was placed on the cartridge, and the catalyst and base mixed by co-extrusion through the mixing tip. A Kenics static mixer consists of a circular pipe within which are fixed a series of short helical elements of alternating left- and right-hand pitch. The helical design of the central element causes a transverse flow to arise in the plane normal to the pipe axis. As a consequence, radial mixing of the two compositions is achieved. A complete description of the fluid mechanics of a Kenics static mixer may be found on pages 327 and 328 of *Fundamentals of Polymer Processing*, by Stanley Middleman. The silicone compound begins to react (i.e., crosslink) upon admixture of the two compositions.

The quantity of hydrogen gas evolved at 2 hours was measured according to the HYDROGEN GAS EVOLUTION VALUE test described above. After 2 hours from the start of extrusion of the impression material sample through the static mixer, two 0.5 mL samples of gas were removed from the flask using a 0.5 mL Precision gas-tight syringe (Precision Sampling Corp., Baton Rouge, La.) and injected into the sample side of the GC within 2 minutes of each other. For run nos. C-2 through 15, the peak areas for two impression material sample injections were averaged and reported in mL of $H_2$ per 10.0 g of impression material at 2 hours and are set out below in Table 2. For run no. C-1, the value reported in Table 2 is the average of 5 runs (10 injections).

For determination of number of pits in the positive model, the material of each run was extruded through a static mixer into two stainless steel molds each containing three cylindrical cavities that were 25 mm in diameter and 5 mm in depth. A 10 mm×10 mm square had been etched into the base of the mold to provide a defined region for evaluating the pits in subsequently poured die stone. After filling the cavities with impression material, each mold was capped with a stainless steel bar, clamped shut, and placed in a 37° C. bath. After 3 minutes in the bath, the mold was removed, opened, and the impression material disks removed. 3M™ Tray Adhesive (from 3M) was applied to each cured impression material disk and the 6 disks were glued to the bottom of an aluminum pan. Either immediately (<5 min), 30 minutes, or 2 hours after removal from the water bath, a plaster slurry prepared from 150 g gypsum (Jade Stone™ Green, WhipMix Corp) and 33 mL water was poured into the pan to a depth of about 10 mm above the top of the disks. The pan was placed on a vibrating plate for 2 minutes and the plaster allowed to cure for 60 minutes. The plaster was then removed from the pan and the 6 cylindrical depressions evaluated for pits. The number of pits in the positive models resulting from plaster independently poured in less than 5 minutes, 30 minutes or 2 hours after the silicone disks were removed from the water bath were rated with the naked eye and/or with a magnifying glass. If pits were observed easily with the naked eye, the positive models were rated unacceptable ("−"). If no pits were observed with the naked eye, the positive models were examined using a magnifying glass with an average of >5 pits per positive model rated as acceptable ("+") and <5 pits per positive model rated as excellent ("++").

TABLE 2

| Run No. | Palladium Additive in Catalyst Paste | | | mL H$_2$ 2 hrs. | Pits in Positive Model Poured In | | |
|---|---|---|---|---|---|---|---|
| | Additive | Parts | ppm | | <5 min. | 30 min. | 2 hrs. |
| C-1 | None | 0 | 0 | 0.86 | − | − | − |
| C-2 | Pd powder[1] | 0.006 | 20 | 0.68 | − | − | − |
| C-3 | Pd powder | 0.012 | 40 | 0.49 | − | − | − |
| C-4 | Pd powder | 0.024 | 80 | 0.50 | − | + | + |
| C-5 | Pd powder | 0.036 | 120 | 0.39 | + | ++ | ++ |
| 1 | Pd(acac)$_2$[2] | 0.008 | 9 | 1.51 | nr* | nr | − |
| 2 | Pd(acac)$_2$ | 0.017 | 19 | 0.88 | − | + | ++ |
| 3 | Pd(acac)$_2$ | 0.035 | 40 | 0.63 | − | ++ | ++ |
| 4 | Pd(acac)$_2$ | 0.075 | 87 | ne | ++ | ++ | ++ |
| 5 | PdCl$_2$COD[3] | 0.016 | 20 | 0.18 | ++ | ++ | ++ |
| 6 | PdCl$_2$COD | 0.024 | 30 | 0.12 | ++ | ++ | ++ |
| 7 | PdCl$_2$COD | 0.032 | 40 | 0.12 | ++ | ++ | ++ |
| 8 | Pd$_2$BzA$_3$[4] | 0.053 | 40 | 0.03 | ++ | ++ | ++ |
| 9 | PdCl$_2$ACN$_2$[5] | 0.030 | 40 | 0.03 | ++ | ++ | ++ |
| 10 | pdBr$_2$[6] | 0.030 | 40 | 0.10 | ++ | ++ | ++ |
| 11 | PdOAc$_2$[7] | 0.025 | 40 | 0.55 | − | − | ++ |
| 12 | PdCl$_2$[8] | 0.005 | 10 | 1.01 | − | − | − |
| 13 | PdCl$_2$ | 0.010 | 20 | 0.17 | − | ++ | ++ |
| 14 | PdCl$_2$ | 0.015 | 30 | 0.04 | − | ++ | ++ |
| 15 | PdCl$_2$ | 0.020 | 40 | 0.03 | + | ++ | ++ |

[1]Submicron sized palladium powder, Strem product 93-4632.
[2]Palladium (II) acetylacetonate, Strem product 46-1800.
[3]Dichloro(1,5-cyclooctadiene)palladium (II), Strem product 46-0650.
[4]Tris(dibenzylideneacetone)dipalladium (O), Strem product 46-3000.
[5]Dichlorobis(acetonitrile)palladium (II), Strem product 46-0370.
[6]Palladium (II) bromide, Strem product 46-1836.
[7]Palladium (II) acetate, Strem product 46-1780.
[8]Palladium (II) chloride, Strem product 46-1850.
*Not rated.

The data in Table 2 show the effectiveness of palladium compounds in absorbing hydrogen gas in silicone impression material compositions. The incorporation of various types and amounts of palladium compounds in impression materials was effective in minimizing the quantity of hydrogen evolved from the impression material in 2 hours. The effectiveness of the palladium compounds was likewise evident in the reduction in the number of pits in the positive model prepared in various time periods after cure of the impression materials. Run nos. 1–15 exhibit the superior results obtained by using a palladium compound in the silicone dental composition compared to run no. C-1 which containied no palladium and run nos. C-2 through C-5 which contained finely divided palladium powder. The results also show that the palladium compounds were effective at palladium levels as low as 20 ppm of palladium in the catalyst paste (run nos. 5 and 13) while finely divided palladium metal powder at palladium levels of 80–120 ppm was required to be effective (run nos. C-4 and C-5).

The quantity of hydrogen gas evolved at specified times in addition to the 2 hour time period set out in Table 2 was measured according to the HYDROGEN GAS EVOLUTION VALUE test described above. These measurements are set out in Table 3. At the time interval specified in Table 3, two 0.5 mL samples of gas were removed from the flask using a 0.5 mL Precision gas-tight syringe (Precision Sampling Corp., Baton Rouge, La.) and injected into the sample side of the GC within 2 minutes of each other. For run nos. C-2 through 15, the peak areas for two impression material sample injections were averaged and reported in mL of H$_2$ per 10.0 g of impression material at the times specified. For run no. C-1, the value reported in Table 3 is the average of 5 runs (10 injections).

TABLE 3

| Run No. | TIME (Hours) | | | | | | |
|---|---|---|---|---|---|---|---|
| | 0.3 | 0.7 | 1.0 | 1.5 | 3.5 | 6.5 | 23.0 |
| C-1 | 0.08 | 0.29 | 8.25 | 0.69 | 1.22 | 1.63 | 2.47 |
| C-2 | n.i.* | 0.22 | 0.34 | 0.52 | 2.51 | 1.21 | 1.82 |
| C-3 | n.i. | 0.14 | 0.25 | 0.37 | 0.77 | 1.09 | 1.66 |
| C-4 | n.i. | 0.12 | 0.21 | 0.34 | 0.70 | 0.93 | 1.25 |
| C-5 | n.i. | n.i. | 0.18 | 0.26 | 0.58 | 0.79 | 0.88 |
| 1 | n.m.** | n.m. | n.m. | 1.30 | 1.63 | n.m. | n.m. |
| 2 | n.m. | n.m. | n.m. | 0.70 | 0.92 | n.m. | n.m. |
| 3 | n.m. | n.m. | n.m. | 0.53 | 0.76 | n.m. | n.m. |
| 4 | n.m. | n.m. | n.m. | n.m. | n.m. | n.m. | n.m. |
| 5 | n.i. | n.i. | n.i. | 0.13 | 0.30 | 0.58 | 0.87 |
| 6 | n.i. | n.i. | n.i. | n.i. | 0.21 | 0.35 | 0.53 |
| 7 | n.i. | n.i. | n.i. | n.i. | 0.19 | 0.37 | 0.50 |
| 8 | n.i. | n.i. | n.i. | n.i. | n.i. | 0.15 | 0.39 |
| 9 | n.i. | n.i. | n.i. | n.i. | n.i. | 0.13 | 0.19 |
| 10 | n.i. | n.i. | n.i. | n.i. | 0.22 | 0.33 | 0.44 |
| 11 | n.i. | 0.13 | 0.25 | 0.43 | 0.86 | 1.20 | 1.52 |
| 12 | 0.12 | 0.40 | 0.59 | 0.85 | 1.22 | 1.38 | 1.58 |
| 13 | n.i. | n.i. | n.i. | 0.11 | 0.22 | 0.27 | 0.39 |
| 14 | n.i. | n.i. | n.i. | n.i. | 0.11 | 0.16 | 0.30 |
| 15 | n.i. | n.i. | n.i. | n.i. | 0.11 | 0.16 | 0.29 |

*Not integrated; the integrator on the GC was not sensitive enough to integrate a peak less than about 0.12 mL of H$_2$.
**Not measured.

The data in Table 3 show the effectiveness of a number of palladium compounds at various concentrations (run nos. 1–15) in absorbing hydrogen gas evolved from silicone impression material compositions at certain time intervals. The compositions of run nos. 5–10 and 13–15 exhibited particularly low amounts of hydrogen gas evolution.

EXAMPLE 2

An impression was made of a "TYPODONT" model (from Columbia Dentoform Corp.) using the composition of C-1 in Table 2. The material was extruded through a static mixer into an impression tray and applied to the Typodont model. After about 5 minutes, the impression was removed from the typodont model and immediately a 0.1 percent palladium (II) chloride suspension in ethanol was brushed onto the surface of the impression in an amount sufficient to wet the entire surface. The surface was allowed to dry and about 10 minutes after application of the suspension, a plaster slurry made by combining 23 parts water and 100 parts gypsum was poured into the impression and allowed to set for about 60 minutes. The positive model was then removed from the impression and visually inspected for pits. The positive model showed no pits.

The above procedure was repeated, except that PdCl$_2$COD was used instead of PdCl$_2$. The resultant positive model showed no pits.

As a control, the above procedure was repeated, except that no palladium compound suspension was applied to the impression surface prior to preparing the positive model. The cured positive model showed numerous pits.

EXAMPLE 3

As a control, an impression was prepared as described for the control in Example 2 with no palladium compound applied to the impression surface prior to preparing the positive model. A plaster slurry was prepared by combining 100 parts gypsum with a sonically dispersed suspension of 0.062 parts palladium (II) chloride and 23 parts water. The slurry was poured into the impression, allowed to cure for about 60 minutes and removed. The positive model was visually inspected and showed numerous pits.

The above procedure was repeated, except that PdCl$_2$COD was used instead of PdCl$_2$. The resultant positive model showed no pits.

We claim:

1. A composition comprising:
   a) an addition-curable compound;
   b) a crosslinker;
   c) a platinium containing catalyst; and
   d) an inorganic, organic or organometallic compound of palladium in an amount effective to reduce the amount of hydrogen gas evolved in the reaction of said composition.

2. A composition according to claim 1, wherein said compound of palladium is present in an amount such that the Hydrogen Gas Evolution Value of said composition in 2 hours per 10.0 g of the composition is less than about 0.6 mL.

3. A composition according to claim 2, wherein the Hydrogen Gas Evolution Value in 2 hours per 10.0 g of the composition is less than about 0.4 mL.

4. A composistion according to claim 2, wherein the Hydrogen Gas Evolution Value in 2 hours per 10.0 g of the composition is less than about 0.2 mL.

5. A composition according to claim 1, wherein said amount of said compound of palladium is sufficient to provide a positive gypsum model that is substantially free of pits.

6. A composition according to claim 1, wherein said compound of palladium is selected from the group consisting of palladium halides, complexes of palladium with an organic acid, complexes of palladium with β-diketones, complexes of a palladium halide with an amine, complexes of palladium and a phosphine, complexes of a palladium halide with a nitrogen compound, and complexes of palladium with an olefin.

7. A composition according to claim 1, wherein said addition-curable compound comprises a vinyl-containing organopolysiloxane.

8. A composition according to claim 1, wherein said crosslinker comprises an organohydrogenpolysiloxane containing a multiplicity of SiH bonds.

9. A composition according to claim 1, wherein said catalyst comprises a Karstedt platinum catalyst.

10. A composition according to claim 1, wherein said compound of palladium is selected from the group consisting of palladium (II) acetylacetonate, dichloro(1,5-cyclooctadiene)palladium (II), tris(dibenzylideneacetone)dipalladium (O), dichlorobis(acetonitrile)palladium (II), palladium (II) bromide, palladium (II) acetate, and palladium (II) chloride.

11. A composition according to claim 1, wherein said amount of said compound of palladium is from about 1 to about 500 ppm of the total composition based on palladium as the element.

12. A composition according to claim 1, wherein said amount of said compound of palladium is from about 5 to 200 ppm of the total composition based on palladium as the element.

13. A composition according to claim 1, wherein said amount of said compound of palladium is from about 10 to 100 ppm of the total composition based on palladium as the element.

14. A composition according to claim 1, wherein the composition is a dental impression material.

15. A composition according to claim 1, further comprising a filler present in the composition between about 20 and 80 weight percent.

16. A composition according to claim 1, wherein said addition-curable compound is present in about 20 to 90 weight percent, said crosslinker is present in about 0.2 to 20 weight percent, said catalyst is present in about 20 to 500 ppm and said compound of palladium is present in about 5 to 200 ppm of the total composition based on palladium as the element.

17. A method of making a positive dental model comprising the steps of a) preparing an impression using a hardenable composition, said composition comprising (i) an addition-curable compound; (ii) a crosslinker; (iii) a platinum containing catalyst; and (iv) an inorganic, organic or organometallic compound of palladium in an amount effective to reduce the amount of hydrogen gas evolved in the reaction of said composition, and b) preparing the positive model from said impression.

18. A method according to claim 17, wherein the compound of palladium is present in an amount such that the Hydrogen Gas Evolution Value in 2 hours per 10.0 g of the composition is less than about 0.6 mL.

19. A method according to claim 18, wherein the Hydrogen Gas Evolution Value in 2 hours per 10.0 g of the composition is less than about 0.4 mL.

20. A method according to claim 18, wherein the Hydrogen Gas Evolution Value in 2 hours per 10.0 g of the composition is less than about 0.2 mL.

21. A method according to claim 17, wherein said amount of said compound of palladium is sufficient to provide a positive gypsum model that is substantially free of pits.

22. A method according to claim 17, wherein said compound of palladium is selected from the group consisting of palladium halides, complexes of palladium with an organic acid, complexes of palladium with β-diketones, complexes of a palladium halide with an amine, complexes of a palladium halide with a nitrogen compound and complexes of palladium with an olefin.

23. A method according to claim 17, wherein said addition-curable compound comprises a vinyl-containing organopolysiloxane.

24. A method according to claim 17, wherein said crosslinker comprises an organohydrogenpolysiloxane containing a multiplicity of SiH bonds.

25. A method according to claim 17, wherein said catalyst comprises a Karstedt platinum catalyst.

26. A method according to claim 17, wherein said compound of palladium is selected from the group consisting of palladium (II) aceylacetonate, dichloro(1,5-cyclooctadiene)palladium (II), tris(dibenzylideneacetone)dipalladium (O), dichlorobis-(acetonitfile)palladium (II), palladium (II) bromide, palladium (II) acetate, and palladium (II) chloride.

27. A method according to claim 17, wherein said amount of said compound of palladium is about 1 to about 500 ppm of the total composition based on palladium as the element.

28. A method according to claim 17, wherein said amount of said compound of palladium is about 5 to 200 ppm of the total composition based on palladium as the element.

29. A method according to claim 17, wherein said amount of said compound of palladium is about 10 to 100 ppm ofthe total composition based on palladium as the element.

30. A method according to claim 17, further comprising a filler present in the composition between about 20 and 90 weight percent.

31. A method of making a positive dental model comprising the step of applying an inorganic, organic or organometallic compound of palladium over at least part of the surface of an impression that will contact a positive model material before pouring said model material, said compound of palladium being present in an amount such that the positive model is substantially free of pits.

32. A melhod according to claim 31, wherein said positive model material comprises gypsum.

33. A method of making a positive dental model comprising the step of scavenging hydrogen gas escaping from an impression by mixing an inorganic, organic or organometallic compound of palladium with a hardenable positive model material prior to pouring said model material, said compound of palladium being present in an amount such that the positive model is substantially free of pits.

34. A method according to claim 33, wherein said positive model material comprises gypsum.

* * * * *